US012810974B2

(12) United States Patent
Schoonbroodt

(10) Patent No.: US 12,810,974 B2
(45) Date of Patent: Nov. 24, 2026

(54) PROCESS AND SYSTEM FOR INITIATING AND MONITORING AN ORTHODONTIC TREATMENT

(71) Applicant: Dental Center SPRL, Liege (BE)

(72) Inventor: Martin Maria Ghislain Schoonbroodt, Liege (BE)

(73) Assignee: Dental Center SPRL, Liege (BE)

( * ) Notice: Subject to any disclaimer, the term of this patent is extended or adjusted under 35 U.S.C. 154(b) by 197 days.

(21) Appl. No.: 18/265,137

(22) PCT Filed: Nov. 29, 2021

(86) PCT No.: PCT/EP2021/083378

§ 371 (c)(1),
(2) Date: Jun. 2, 2023

(87) PCT Pub. No.: WO2022/117506

PCT Pub. Date: Jun. 9, 2022

(65) Prior Publication Data

US 2024/0029837 A1 Jan. 25, 2024

(30) Foreign Application Priority Data

Dec. 3, 2020 (BE) .................................. 2020/5875

(51) Int. Cl.

| | |
|---|---|
| ***G16H 10/20*** | (2018.01) |
| ***A61C 7/00*** | (2006.01) |
| ***G06T 1/00*** | (2006.01) |
| ***G06T 7/00*** | (2017.01) |
| ***G16H 10/60*** | (2018.01) |

(52) U.S. Cl.

CPC ............. *G16H 10/20* (2018.01); *A61C 7/002* (2013.01); *G06T 1/0007* (2013.01); *G06T 7/0012* (2013.01); *G16H 10/60* (2018.01); *G06T 2207/20081* (2013.01); *G06T 2207/30036* (2013.01)

(58) Field of Classification Search

None

See application file for complete search history.

(56) References Cited

U.S. PATENT DOCUMENTS

| | | | | |
|---|---|---|---|---|
| 6,471,512 | B1 | 10/2002 | Sachdeva | |
| 6,512,994 | B1 | 1/2003 | Sachdeva | |
| 2002/0064302 | A1* | 5/2002 | Massengill | G16H 40/67 712/225 |
| 2008/0306724 | A1* | 12/2008 | Kitching | A61C 7/00 704/2 |
| 2012/0148975 | A1* | 6/2012 | Brawn | A61C 7/06 433/29 |
| 2014/0088607 | A1* | 3/2014 | Recknor | A61B 5/1071 606/102 |
| 2016/0228213 | A1* | 8/2016 | Tod | G16H 10/20 |
| 2018/0125610 | A1* | 5/2018 | Carrier, Jr. | A61C 7/002 |
| 2018/0153648 | A1* | 6/2018 | Shanjani | B29C 64/393 |
| 2018/0368943 | A1* | 12/2018 | Katzman | A61C 9/0006 |
| 2019/0175303 | A1 | 6/2019 | Akopov et al. | |
| 2019/0231492 | A1* | 8/2019 | Sabina | G06T 19/00 |
| 2019/0350680 | A1 | 11/2019 | Chekh et al. | |
| 2020/0066391 | A1 | 2/2020 | Sachdeva et al. | |

(Continued)

FOREIGN PATENT DOCUMENTS

| | | | | |
|---|---|---|---|---|
| CA | 2292141 | A1 * | 6/2001 | G06F 19/3418 |
| EP | 3671756 | A1 | 6/2020 | |
| WO | 2020112735 | A2 | 6/2020 | |

OTHER PUBLICATIONS

Specification of U.S. Appl. No. 62/975,148 (Year: 2020).*

WIPO, International Search Report for PCT/EP2021/083378, Feb. 7, 2022.

*Primary Examiner* — Heidi M Eide

(74) *Attorney, Agent, or Firm* — Hodgson Russ LLP

(57) ABSTRACT

The current invention relates to a process for initiating and monitoring an orthodontic treatment, comprising the following steps: a. Collecting initial data of a subject requiring orthodontic treatment by means of an online questionnaire during an initial digital consultation, said digital data comprises at least a digital image of the subject's teeth, a description of the orthodontic problem and personal information regarding the subject. b. Obtaining further data from said subject during a physical consultation wherein said further data, next to other records, comprise intra-oral image data generated from the oral cavity of the selected patient; and c. analysing said intra-oral image data and providing an initial orthodontic treatment scheme for said subject based on said analysis of data, said initial orthodontic treatment scheme comprises treatment steps in order to obtain a desired orthodontic result and an orthodontic progression estimate; and d. initiating said initial treatment scheme for said subject, e. wherein the follow up and/or implementation of said treatment scheme in said subject is performed at least partially in a digital manner, comprising one or more digital treatment consults, wherein during said digital treatment consult, said subject provides intra-oral image data via a digital platform to a practitioner and wherein said intra-oral image data uploaded to said digital platform is compared with said orthodontic progression estimate, and said treatment scheme is maintained or amended based on said matching comparison. The current invention also relates to a system for the monitoring of an orthodontic treatment.

9 Claims, No Drawings

(56) References Cited

U.S. PATENT DOCUMENTS

| | | | | |
|---|---|---|---|---|
| 2020/0405447 | A1* | 12/2020 | Salah | A61C 13/34 |
| 2021/0068745 | A1* | 3/2021 | Yancey | A61B 5/004 |
| 2021/0244502 | A1* | 8/2021 | Farkash | A61C 7/002 |
| 2022/0030162 | A1* | 1/2022 | Cramer | A61B 1/24 |
| 2023/0149135 | A1* | 5/2023 | Lipnik | A61C 9/0053<br>433/214 |
| 2023/0404709 | A1* | 12/2023 | Giegerich | A61B 1/247 |

* cited by examiner

PROCESS AND SYSTEM FOR INITIATING AND MONITORING AN ORTHODONTIC TREATMENT

FIELD OF THE INVENTION

The present invention relates to a process for initiating and monitoring an orthodontic treatment. In a second aspect, the present invention also relates to a system for the monitoring of an orthodontic treatment.

BACKGROUND

Orthodontics is a specialty of dentistry that is concerned with improvement of the general appearance of a patient's teeth and also the correction of malocclusions, crookedness and other flaws of the teeth. This goal is achieved by means of one or more orthodontic appliances such as brackets, aligners or retaining structures. Often, such orthodontic appliances are periodically adjusted by the dental practitioner to help align and straighten the teeth.

Indeed, in the field of orthodontics, orthodontic treatment is an iterative process requiring multiple adjustments to the orthodontic appliances in order to reposition the teeth and by doing so correcting flaws and improving the general appearance of the patient. U.S. Pat. No. 6,471,512 for instance, describes a method for the treatment of an orthodontic patient. In addition, US 2019/175303 describes orthodontic treatment planning using a series of patient-removable appliances (e.g., aligners) to reposition the teeth.

However, as the orthodontic treatment often requires multiple months or years to be completed, the follow-up by a physical consultation of each of these adjustments over this extended period of time is cumbersome. This is especially inconvenient for the patient as he loses a lot of time by traveling back and forth to the consultation bureau of the orthodontist and waiting in the waiting room before the start of the appointment.

Likewise, before the start of the treatment, a subject must visit a practitioner to receive information to know whether the practitioner is able to perform a certain orthodontic treatment on the subject or not. In certain cases, the orthodontist is not able to help the subject, resulting in an unnecessary appointment, costing both the subject and the practitioner valuable time.

The aim of the invention is to provide an improved process for initiating and monitoring an orthodontic treatment, wherein this process is able to reduce the number of unnecessary physical consultations, saving time, both for the subject and the practitioner.

SUMMARY OF THE INVENTION

The present invention and embodiments thereof serve to provide a solution to one or more of above-mentioned disadvantages.

To this end, the present invention relates to a process. More in particular, the present disclosure provides a process for initiating and monitoring an orthodontic treatment, comprising the following steps:

a. Collecting initial data of a subject requiring orthodontic treatment by means of an online questionnaire during an initial digital consultation, said digital data comprise at least a digital image of the subject's teeth, a description of the orthodontic problem and personal information regarding the subject.

b. Obtaining further data from said subject during a physical consultation wherein, next to other records, said further data comprise intra-oral image data generated from the oral cavity of the selected patient; and
c. analysing said intra-oral image data and providing an initial orthodontic treatment scheme for said subject based on said analysis of data, said initial orthodontic treatment scheme comprises treatment steps in order to obtain a desired orthodontic result and an orthodontic progression estimate; and
d. initiating said initial treatment scheme for said subject,
e. wherein the follow up and/or implementation of said treatment scheme in said subject is performed at least partially in a digital manner, comprising one or more digital treatment consults, wherein during said digital treatment consult, said subject provides intra-oral image data via a digital platform to a practitioner and wherein said intra-oral image data uploaded to said digital platform is compared with said orthodontic progression estimate, and said treatment scheme is maintained or amended based on said matching comparison.

Preferred embodiments of the process are described herein.

A specific preferred embodiment relates to an invention described herein.

In a second aspect, the present invention relates to a system. More particular, the disclosure as described herein provides a system for the monitoring of an orthodontic treatment comprising a smartphone application for obtaining intra-oral image data by the patient, a cloud for online storage and processing of the image data, a dashboard comprising patient data accessible for a practitioner and a machine learning model configured to analyse intra-oral image data provided by a subject in need of an orthodontic treatment to said smartphone application in view of an orthodontic progression estimate comprising one or more orthodontic models of said subject.

Preferred embodiments of the system are described herein.

The process according to the present disclosure is able to diminish the number of unnecessary physical consultations. Firstly, by providing an online questionnaire during an initial digital consultation which enables a first preselection of subjects suited for the orthodontic treatment. And additionally, by providing follow up and/or implementation of said treatment in said subject at least partially in a digital manner.

DETAILED DESCRIPTION OF THE INVENTION

The present invention concerns a process for initiating and monitoring an orthodontic treatment, a system for monitoring an orthodontic treatment and a use of the aforementioned process or system in the treatment of an intra-oral condition in need of orthodontic treatment.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

The term "image data" may include digital data that represents, defines or renders a viewable 3D image, or the image itself. In the examples below, the terms "digital image" and "image data" are used interchangeably.

"A", "an", and "the" as used herein refers to both singular and plural referents unless the context clearly dictates otherwise. By way of example, "a compartment" refers to one or more than one compartment.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

"Gingivitis" as used herein, refers to a non-destructive disease that causes inflammation of the gums. The most common form of gingivitis is in response to bacterial biofilms (also called plaque) that is attached to tooth surfaces, termed plaque-induced gingivitis. Most forms of gingivitis are plaque-induced. While some cases of gingivitis never progress to periodontitis, periodontitis is always preceded by gingivitis. "Periodontitis" as used herein, refers to a disease in which the inflammation of the gums results in tissue destruction and bone resorption around the teeth. Gingivitis is reversible with good oral hygiene; however, without treatment, gingivitis can progress to periodontitis. Periodontitis can ultimately lead to tooth loss.

A "malocclusion" as described herein, refers to a misalignment or incorrect relation between the teeth of the two dental arches when they approach each other as the jaws close.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments of the invention described herein are capable of operation in other sequences than described or illustrated herein.

The recitation of numerical ranges by endpoints includes all numbers and fractions subsumed within that range, as well as the recited endpoints.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention. The terms or definitions used herein are provided solely to aid in the understanding of the invention.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In a first aspect the invention relates to a process for initiating and monitoring an orthodontic treatment, comprising multiple steps, which are summarized here below. A first step comprises collecting initial data of a subject requiring orthodontic treatment by means of an online questionnaire during an initial digital consultation, said digital data comprise at least a digital image of the subject's teeth, a description of the orthodontic problem and personal information regarding the subject.

In an embodiment, the digital image of the subject's teeth is at least a front view of the mouth of the subject and preferably a complementary set of pictures with lateral views, wherein the subject smiles with clenched teeth. Occlusal open mouth views may complete the set of images. In an embodiment, the description of the orthodontic problem is provided by selecting a certain picture from a list of pictures depicting common orthodontic problems, such as a collision of teeth, an excess overbite, a crossbite, a diastema or an open bite. In a preferred embodiment, the personal information regarding the subject comprises at least the gender, the age category and the contact information of the subject.

In a preferred embodiment, said initial data is collected through an online questionnaire by means of a smartphone application or a web application. In a preferred embodiment, the smartphone or web application is programmed to operate in various operating systems (e.g., Symbian, iOS, Android and webOS).

In a preferred embodiment a practitioner will decide based on said initial data of said subject whether or not an orthodontic treatment is advised. Based on the data obtained from the online questionnaire, the orthodontist can decide whether or not the patient is suited for the orthodontic treatment. By pre-screening patients by means of an initial digital consultation, patients that are not suited for the treatment are saved a trip to the consultation office. In addition, the orthodontist saves time by a reduction in unnecessary appointments. Furthermore, pre-screening subjects reduces the waiting time for subjects who actually need treatment, those subjects will be able to get an appointment and, subsequently, receive treatment, faster. Given the shortage of practising orthodontists and the resulting long waiting lists for new patients, this initial digital consultation, which enables to significantly reduce the number of unnecessary appointments, is highly advantageous, both for the patients and the practitioners. In addition, reducing the number of unnecessary appointments is not only favourable in view of time management, but is also advantageous to minimize the number of subjects the physician (and staff working there) comes in to contact with, reducing the risk of coming into contact with subjects who might be ill and spread diseases, a factor important to take into account in the current pandemic state.

Patients that fulfill the requirements for the orthodontic treatment are invited for a physical consultation.

In a second step further data from said subject is obtained during a physical consultation. Said further data comprise amongst others intra-oral image data generated from the oral cavity of the selected patient. Such a physical consultation is important to allow the subject to discuss his or her expectations, remarks, hesitations and/or questions face-to-face with the physician. Although digital consultations provide many benefits, it might form a barrier between the patient and the physician, possibly resulting in loss of important information regarding the treatment. By providing a process that includes this physical consultation and is not limited to digital consultations only (the latter being the case in the process of US 2020/066391 which describes a computer-implemented system for providing an orthodontic care management solution not including an initial digital consultation), the treatment quality is highly improved.

Said intra-oral image data can be generated by any means known from the state of the art, such as light-based scanning, contact probing, active wavefront sampling, X-ray radiography, magnetic resonance imaging, ultrasound imaging, computerized tomography, scanning a bite impression, performing a low resolution scan, or performing a (partial) intra-oral digital scan.

In a preferred embodiment the intra-oral image data is obtained during the physical consultation by means of an intra-oral digital scanner. The intra-oral digital scanner provides accurate data in a fast manner. In addition, the use of an intra-oral digital scanner for generating intra-oral image data is found to be less invasive and less painful for the patient then the acquirement of an impression of the patient's teeth via an impression mechanism using specific materials. In addition, by using an intra-oral imaging system such as an oral scanner, there is no requirement anymore to convert the impression to digital images.

In a next step said intra-oral image data is analysed and an initial orthodontic treatment scheme for said subject based on said analysis of data is provided.

In an embodiment, the analysis includes the conversion of the intra-oral image data (the scanned image) of the patient's orthodontic anatomy into a digital three-dimensional (3-D) model of the patient's malocclusions. Such a conversion is done by receiving the scanned image of the patient's orthodontic anatomy, x-rays of the relevant patient's anatomy, photographs, and/or other patient information and generating the 3-D digital model therefrom. Such a conversion process is described in U.S. Pat. No. 6,512,994, entitled "Method and Apparatus for Producing a Three-Dimensional Digital Model of an Orthodontic Patient".

Said initial orthodontic treatment scheme comprises treatment steps in order to obtain a desired orthodontic result and an orthodontic progression estimate.

While the movement of teeth may occur throughout the course of treatment, movement does not usually occur in a smooth continuous fashion. Sometimes there are "bottlenecks" that impede, or even stall, tooth movement. For example, certain teeth may need to be moved out of the way to create space for other teeth. Delays may also develop because of anchorage loss or undesirable tooth movement that must be remedied before proceeding further. Moreover, certain teeth may simply move slower than others, based on the unique biology of each patient's dental anatomy. The treating practitioner, typically an orthodontist, can anticipate some of these challenges when formulating a treatment scheme for the patient comprising multiple treatment steps.

In an embodiment, said progression estimate comprises one or more digital orthodontic models of said subject's orthodontic anatomy, said orthodontic models comprise a model of the subject's final desired orthodontic result and one or more models of intermediate orthodontic results.

In a preferred embodiment, said orthodontic models are three-dimensional (3-D) digital models.

These 3-D digital orthodontic models are a visual representation of the different steps in the treatment scheme and are necessary to compare with the intra-oral image data obtained during the digital consultation in order to make a decision regarding the next steps in the treatment scheme.

In an embodiment, a morphing technique is performed to render an immediate result simulation. Such a simulation can for instance be discussed during a physical consultation, allowing the patient to more freely discuss his or her expectations, remarks, hesitations and/or questions face-to-face with the physician.

Different morphing approaches exist and these can be used to find out an approximate solution to represent the empirical outcome. The morphing tool produces soft tissue contouring from hard tissue movements to simulate the changes in shape that the dental arch performs. This gives both the orthodontist and the patient freedom to explore and verify in practice the temporal evolution of the planned treatment. In an embodiment, this morphing technique simulates the smile of the patient to be obtained after the orthodontic treatment. A simulation of the envisioned orthodontic result can be incorporated at the height of the dental arches in a frontal view of the patient's smiling face. By incorporating a simulation of the envisioned orthodontic result in a digital image of the patient's face, not only the effect of the orthodontic treatment on the level of the teeth, but also on the level of the face in total of the patient can be simulated. The orthodontic treatment will not only have an effect on the teeth, but also on the overall facial appearance of the patient. By correcting flaws in the orthodontic anatomy, the ratio of the smile to other features of the face can be changed. In a preferred embodiment, the orthodontic treatment optimizes the facial symmetry of the patient. This is desired, given that a balanced facial symmetry is perceived as more appealing.

This simulation can be shown to the patient, for instance during a first physical consultation, and can help the patient to visualize the intended result of the orthodontic treatment. During this consultation the patient can discuss his or her expectations, remarks, hesitations and/or questions face-to-face with the physician. In an embodiment, this morphing technique can be performed at the end of the treatment, to compare the initial appearance of the patient with the obtained appearance after treatment.

In an embodiment, the progression estimate is used to develop the orthodontic appliance(s) by using software specifically designed for this purpose. In an embodiment, the resulting designs are sent via internet to a manufacturer of orthodontic appliances, which will produce the patient-tailored orthodontic appliance(s). Upon receipt of the orthodontic appliance(s), the orthodontist, in most cases, subsequently installs it, thereby initiating the treatment scheme.

During the follow up and/or implementation of said treatment scheme in said subject, taking a full dental impression or a high-resolution intraoral scan is time-consuming and uncomfortable to the patient.

Hence, in a preferred embodiment, the follow up and/or implementation of said treatment scheme in said subject is performed at least partially in a digital manner, comprising one or more digital treatment consults, wherein during said digital treatment consult, said subject provides intra-oral image data via a digital platform to a practitioner. In an embodiment said digital platform is a smartphone application. In another embodiment, said digital platform is a web application.

Because the follow up and/or implementation of said treatment scheme in said subject is performed at least partially in a digital manner, the number of physical consultations is significantly reduced. This is more favorable for the patient, saving time and money by reducing traveling back and forth to the consultation office. And evenly important, this allows the orthodontist to monitor the progress of the treatment more frequently and adjust the treatment scheme faster, significantly reducing the therapy time. In addition, by arranging the follow up and/or implementation of said treatment scheme at least partially in a digital manner, hence, reducing the number of physical appointments, the number of subjects the physician (and staff working there) comes into contact with is minimized, allowing to reduce the risk of coming into contact with subjects who might be ill and spread diseases. In the current pandemic state, this is considered a major advantage.

In an embodiment, the intra-oral image data obtained during the digital treatment consults are obtained by means of a smartphone application on a subject's smartphone, the smartphone comprising a built-in camera. The smartphone application is able to access and make use of the built-in camera of the smartphone. In an embodiment, an extra device for correctly positioning the smartphone can be used by the subject.

Said intra-oral image data uploaded to said digital platform is compared with said orthodontic progression estimate, and said treatment scheme is maintained or amended based on said matching comparison.

After a certain treatment step, a matching result is obtained when the data points from the preset orthodontic 3-D model are in agreement with the according pixels of the intra-oral image data uploaded by the patient.

In an embodiment, the comparison between the uploaded intra-oral image data and the orthodontic progression estimate is solely performed by the practitioner.

Artificial intelligence (AI) is the concept whereby computer systems perform tasks that normally require human intelligence, such as visual perception, speech recognition, decision making and translations form one language to another. One form of artificial intelligence is the development of software that is able to autonomously perform reasoning and solve problems.

In a preferred embodiment, the comparison of the intra-oral image data with the orthodontic progression estimate and the amendment or maintenance of the treatment scheme is performed automatically by means of a machine learning model.

Machine learning is seen as a subset of AI. A machine learning model is a file that has been trained to recognize certain types of patterns. You train a model over a set of data, providing it an algorithm that it can use to reason over and learn from those data. The performance of the algorithms becomes better when more data is provided, in other words, the algorithms improve automatically through experience.

An analytical model has parameters that need to be estimated in order to make good predictions. This translates into finding the optimal parameter values for the analytical model. For this reason, a training set is used to find or to estimate the optimal parameter values. The "training set" is the set of data observations (also called 'examples' or 'instances') that is used to train or to learn the model. Once we have a trained model, we can use it to make predictions.

In an embodiment the training set comprises a database of intra-oral images, comprising more than 170 different clinical situations. These clinical situations are very diverse and range from observations important from on orthodontic view point (for instance loss of attachments, incorrectly aligned aligners, movement of teeth) to more general dental problems, such as poor oral hygiene and periodontal diseases. The images in this training set are firstly correctly classified by highly qualified orthodontists and serve to optimize the algorithm. Because of the huge amount of image data in this training set, the performance of the algorithm is of a very high quality, allowing the correct clinical situation to be correctly detected.

Because of the very diverse range of clinical situations included in the training set, in addition to the effects of the orthodontic treatment, additional data such as oral hygiene and periodontal diseases, such as gingivitis and periodontitis, can be monitored by means of the process.

AI allows quick and reliant performance of tasks, however, to rule out any mistakes made by the deep learning model, it is advisable to review the results obtained by this form of AI by a trained practitioner. Hence, in a preferred embodiment, the result of this deep learning model is verified by a certified practitioner. Human verification of AI results is currently still necessary in many AI implementations and allows to increase the quality of the obtained results.

In an embodiment, the orthodontic treatment is accelerated by means of one or more accelerating orthodontic devices. In a preferred embodiment, these accelerating orthodontic devices are used on a daily routine by the patient at home. By using one or more accelerating orthodontic devices during orthodontic treatment (for instance in combination with bracers or aligners) not only the velocity of tooth movement is accelerated, but also the pain and discomfort for the patient is reduced. By reducing the pain and discomfort caused by the orthodontic treatment, treatment compliance is enhanced, which will have a positive effect on the therapy time. In an embodiment, the therapy time is reduced with 50%, as for instance described in WO 2020/112735. By performing the orthodontic treatment process of the current invention wherein the follow up and/or implementation of the treatment scheme is performed at least partially in a digital manner (allowing the orthodontist to monitor the progress of the treatment more frequently and adjust the treatment scheme faster) and, in a preferred embodiment, is accelerated by means of one or more accelerating orthodontic devices, a highly optimized treatment scheme is provided, significantly reducing the therapy time. In an embodiment, the pain and discomfort associated with treatment is reduced with more than 70%. In an embodiment, the accelerating orthodontic device is coupled to a patient engagement application, further improving the therapy compliance. Teeth move through a process called bone remodeling. When force is applied to the teeth, bone cells (osteoblasts and osteoclasts) are mobilized around the root of the tooth. This cellular response causes changes in the bone surrounding the tooth, enabling orthodontics to guide tooth movement. In an embodiment, the accelerating orthodontic device accelerates the velocity of tooth movement by soft pulse technology. This technology uses small vibrations, called micropulses, to gently accelerate movement of teeth. These precisely calibrated vibrations transmit through the roots of the teeth to the surrounding bone, helping to increase the cellular activity and speeding the rate in which the teeth can move. In an embodiment, this soft pulse device is used for 20 minutes per day during the treatment.

In an embodiment, the accelerating orthodontic device accelerates the velocity of tooth movement by photobiomodulation to stimulate the bone around the teeth. Photobiomodulation uses low intensity near infra-red light (850 nm wavelength) to facilitate bone remodelling on a molecular level without any adverse effects. In an embodiment, this photobiomodulation device is used for 10 minutes per day.

In an embodiment, the intra-oral image data obtained during a digital treatment consult can allow to monitor the switch from baby teeth to adult teeth, which makes it possible to register the moment when a treatment scheme can be initiated.

In another embodiment, the intra-oral image data obtained during a digital treatment consult can allow to monitor a rapid palatal expansion (RPE) treatment scheme. RPE or Rapid Maxillary Expansion (RME) is an expansion technique where expansion of 0.5 mm to 1 mm is achieved each day until the posterior crossbite is relieved. A palatal expander is a device in the field of orthodontics which is used to widen the upper jaw (maxilla) so that the bottom and upper teeth will fit together better. The expander works by turning a key inside the center of the expander. The turn of this key will push the arms of the expander. In some cases, self-opening screws replace the key. Palatal expansion is indicated in cases with a difference in the width of the upper jaw to the lower jaw equal to or greater than 4 mm. Typically this is measured from the width of the outside of the first molars in the upper jaw compared to the lower jaw taking into account that the molars will often tip outward to compensate for the difference. Rapid palatal expansion is also used in cleft palate repair, and to gain room for teeth in patients with moderate crowding of the teeth in the upper jaw. For stability purposes, the palatal expander usually remains in the patient's mouth anywhere between 3-6 months, but this time may vary between patients. During this period the bone fills the gap in the maxilla that was created by the expansion process.

By obtaining intra-oral image data, the orthodontist can monitor the palatal expansion and can advise on the sequential use of the expander.

In another preferred embodiment, the orthodontic treatment, wherein one or more teeth of the patient are moved towards a desired position, is achieved by means of one or more orthodontic appliances selected from brackets, a wire, head gear, rubber band placement, aligners and/or a retaining structure.

Orthodontic braces are devices that are placed on a patient's teeth by a dental practitioner. In an orthodontic brace, wires interact with brackets to move teeth to a desired position. Often, such orthodontic braces are periodically adjusted by the dental practitioner to help align and straighten the teeth. Treatment by the dental practitioner may help in repositioning the teeth to correct flaws and improve the general appearance of the patient.

Another method of orthodontic treatment may use a series of clear, removable teeth aligners as an alternative to orthodontic braces. A series of aligners are successively worn by the patient to reposition the teeth to correct flaws.

Aligners offer patients the aesthetics that they desire, and more comfort than braces. Aligners also allow the dental practitioner to finish the cases with much more ease because aligners do not require the dental practitioners to bend wires or reposition brackets.

In a preferred embodiment, said orthodontic appliances are a set of multiple aligners, wherein a first aligner (or a combination of a first upper and lower aligner, for both the upper and lower dental arch) is worn in the oral cavity of a subject during a first period of time and wherein the effect of the first aligner on the position of the teeth in the oral cavity is recorded by means of intra-oral image data provided by said subject to a digital platform. In a next step, said intra-oral image data is analysed and the practitioner advises said subject on the successive steps in the treatment, being to keep on wearing the first aligner or to start wearing the following aligner, based on the analysis.

In a preferred embodiment, each removable orthodontic aligner has a polymeric shell with a plurality of cavities shaped to receive teeth. Each polymeric shell may be configured so that its tooth-receiving cavity has a geometry corresponding to an intermediate or final tooth arrangement. The patient's teeth are repositioned from their initial tooth arrangement to an intermediate and/or a final tooth arrangement by placing a series of aligners over the patient's teeth. At least one of all the aligners used in a single course of treatment is preferably generated at the beginning of the treatment so that they are available when needed and can be given to the patient when they visit the practitioner during a physical consultation.

It is possible that during the treatment, the initial orthodontic treatment scheme has to be adjusted, for instance in the middle (mid-course correction) or at the end (end-course correction) of the treatment. Often new orthodontic appliances, such as additional aligners, will have to be designed and manufactured to implement the adjusted treatment scheme.

In an embodiment, additional orthodontic appliances, such as mid- or end-course correction aligners and retention splints, can be designed and manufactured based on intra-oral image data obtained during a physical consultation. However, taking a full dental impression or a high-resolution intraoral scan during a physical consultation is time-consuming and uncomfortable for the patient.

By leveraging a full set of dental data already acquired during the initial treatment consultation, only small portions of the dental data are needed to reconstruct the current position of the entire dental anatomy. Hence, often there is no need for a full dental impression using specific materials or a high-resolution intraoral scan, which can only be obtained during a physical consultation.

In another embodiment, additional orthodontic appliances, such as mid- or end-course correction aligners and retention splints, can be designed and manufactured based on intra-oral image data obtained during a digital treatment consultation. By obtaining this intra-oral image data during a digital treatment consultation, the number of physical consultations is significantly reduced. This is more favorable for the patient, saving time and money by reducing traveling back and forth to the consultation office.

The additional aligners can be produced only when needed so that the efficiency of the fabrication process is enhanced.

The patient wears each aligner until the practitioner advises to move to the next step in the treatment scheme. At that point, the patient replaces the current aligner with the next aligner in the series until no more aligners remain. Conveniently, the aligners are generally not affixed to the teeth and the patient may place and replace the aligners at any time during the treatment scheme.

The aligner can fit over all teeth present in the upper or lower jaw. Often, only certain one(s) of the teeth will be repositioned while others of the teeth will provide a base or an anchor region for holding the aligner in place as the aligner applies a resilient repositioning force against the tooth or teeth to be repositioned. In complex cases, however, multiple teeth may be repositioned at some point during the treatment. In such cases, the moved teeth can also serve as a base or anchor region for holding the aligner.

In an embodiment, the effect of the aligner is recorded after a period which lasts between 3 and 14 days. By using accelerating orthodontic devices, the velocity of the tooth movement is accelerated and, by reducing pain and discomfort, the therapy compliance is increased. In an embodiment, especially at the end of the treatment, the effect of the aligner is recorded and analysed after a period of only 3 days. By shortening the period in between two consecutive digital consultations, the treatment can be adjusted more rapidly, resulting in a faster transition towards a new step in the treatment scheme or a faster intervention when the treatment is not going according to the initial treatment scheme. So, by increasing the monitoring frequency, the therapy time can be significantly reduced. Because of the digital monitoring of the intra-oral image data, there is no need for a physical consultation. This is more favorable for the patient, saving time and money by reducing traveling back and forth to the consultation office. And evenly important, this allows the orthodontist to monitor the progress of the treatment more frequently and adjust the treatment scheme faster, significantly reducing the therapy time. In a preferred embodiment, the aligner is worn for 20 to 22 hours a day.

In a preferred embodiment, intra-oral image data can be obtained by the patient and processed by an online platform even after the orthodontic treatment to prevent relapse. This is an important step in the orthodontic treatment process of the current invention. By continuing to analyse intra-oral image data after the end of the treatment period, it is possible to monitor possible unwanted movement of the teeth. When this movement is beyond a certain allowed threshold, the patient can be instructed to restart the orthodontic treatment. In this way relapse of the treatment is prevented and the quality of the treatment process is increased.

In a second aspect, the system relates to a system for the monitoring of an orthodontic treatment comprising a smartphone application for obtaining intra-oral image data by the patient, a cloud for online storage and processing of the image data, a dashboard comprising patient data accessible for a practitioner and a machine learning model configured to analyse intra-oral image data provided by a subject in need of an orthodontic treatment to said smartphone application in view of an orthodontic progression estimate comprising one or more orthodontic models of said subject.

In an embodiment, the dashboard includes an electronic patient section and a user interface section. In an embodiment, the electronic patient section contains the three-dimensional scanned images of the patient, x-rays, clinical exams and measurements, dental history, medical history, patient consent forms, photographs, template entries such as chief complaints, etc., free form entries, and extra data. The online cloud receives and stores the intra-oral patient data of the patient's teeth. In a next step, the machine learning model automatically compares this intra-oral image data with the orthodontic progression estimate and allows to make observations regarding the progression of the treatment or to detect problematic situations, for instance an incorrectly aligned aligner. In a preferred embodiment, every observation made by the machine learning model is first validated by a certified physician to ensure the correctness of the observation.

In a preferred embodiment, the system comprises a communication system for sending messages to a subject. In an embodiment, observations and basic conclusions made by the machine learning model are verified by a certified physician in the initial phase and, as this correlation between digital data and the clinical interpretation made by the machine learning model fits repeatedly, the intervention of the physician becomes obsolete at this level and the verification by the physician of the clinical interpretation made by the machine learning model is not necessary anymore. In an embodiment, the physician has to intervene solely in all new digital data outcomes to interpret them, and ideally, to add them to the automatic answer list. In an embodiment, an automatic message will be drafted and send to the client via the system. The messages can be of any order, for instance text messages, such as email or SMS.

In an embodiment, the text messages comprise reminders, for instance a reminder to upload new intra-oral image data. In an embodiment, the messages comprise instructions for the patient, for instance the instruction to switch from one aligner to the next aligner. In an embodiment, the messages give information to the patient, for instance feedback regarding the intra-oral image data sent by the patient. In an embodiment, the message can contain information regarding a possible problematic situation and might comprise instructions to solve the problematic situation. In a further embodiment, the message comprises instructions to make an appointment for a new physical consultation. In an embodiment the messages are accompanied by additional data, such as photos or videos, for instance explanatory videos comprising instructions. In a preferred embodiment, the messages comprise motivational content in order to enhance the treatment compliance of the patient.

In a preferred embodiment, said smartphone application comprises instructions for generating and storing intra-oral cavity data of said subject.

In an embodiment, the aforementioned process or the aforementioned platform is used in the treatment of an intra-oral condition in need of orthodontic treatment.

In an embodiment the orthodontic treatment is used to correct a collision of teeth. A collision of teeth may be said to occur when there is not enough space between two teeth to allow a tooth to move in between the two teeth. In another embodiment, the orthodontic treatment is used to correct an excess overbite. Overbite medically refers to the extent of vertical (superior-inferior) overlap of the maxillary central incisors over the mandibular central incisors, measured relative to the incisal ridges. In another embodiment, the orthodontic treatment is used to correct an excess underbite (vertical overlap of the mandibular central incisors over the maxillary central incisors, measured relative to the incisal ridges). In another embodiment, the orthodontic treatment is used to correct a posterior crossbite. A posterior crossbite occurs when the front teeth are an overbite, extending over the bottom teeth, but the molars are in underbite, meaning the bottom molars protrude further into the cheek than the top molars. In another embodiment, the orthodontic treatment is used to correct a diastema (a space or gap between two teeth). In another embodiment, the orthodontic treatment is used to correct an anterior open bite. An anterior open bite is when the front and bottom teeth are pushed outward.

The invention is further described by the following non-limiting examples which further illustrate the invention, and are not intended to, nor should they be interpreted to, limit the scope of the invention.

The present invention will be now described in more details, referring to examples that are not limitative.

EXAMPLES

Example 1

A subject suffering from an underbite is looking for an orthodontic treatment. To find a practitioner that can help him, he fills in an online questionnaire on the webpage from a certain practitioner using a web application. From this online questionnaire the practitioner gathers initial data over the subject. During the online questionnaire the subject is asked to upload digital images of the subject's teeth, comprising a front view of the mouth of the subject, wherein the subject smiles with clenched teeth. The subject is also asked to provide various personal information, such as gender, age category and contact information. The subject further provides a description of the orthodontic problem and selects a picture of an underbite from a list of pictures depicting common orthodontic problems. The practitioner reviews this information and decides that the subject is suited to follow the orthodontic treatment. By pre-screening subjects and filtering out those subjects not eligible for treatment, the waiting time for subjects who actually need treatment is reduced. The subject is invited for a physical consultation, during which further data from the subject is obtained, such as intra-oral image data generated from the oral cavity of the selected patient by an intra-oral digital scanner. Afterwards, this intra-oral image data is analysed and an initial orthodontic treatment scheme for the subject based on the analysis of the data is developed. During the analysis the intra-oral image data (the scanned image) of the patient's orthodontic anatomy is converted into a digital 3-D model of the patient's malocclusions. In addition, a morphing technique is performed to render an immediate result simulation, which is discussed during the physical consultation, allowing the patient to freely discuss his or her expectations, remarks, hesitations and/or questions face-to-face with the physician. The practitioner decides to use a set of multiple aligners to treat the underbite of the subject. The initial orthodontic treatment scheme comprises treatment steps in order to obtain a desired orthodontic result and an orthodontic progression estimate. This orthodontic progression estimate comprises one or more digital orthodontic models of said subject's orthodontic anatomy, including a model of the subject's final desired orthodontic result and one or more models of intermediate orthodontic results.

The progression estimate, comprising the various orthodontic models, is used to develop the aligners by using software specifically designed for this purpose. The resulting designs are sent via internet to a manufacturer of aligners, which produces the patient-tailored aligners. The initial treatment scheme for the subject is initiated. A first aligner is worn in the oral cavity of the subject for 22 hours during a period of 7 days. After this period, the effect of the first aligner on the position of the teeth in the oral cavity is recorded by means of intra-oral image data, wherein the subject takes photographs with a smartphone application on his or her smartphone. The intra-oral image data is uploaded to a digital platform and is automatically compared with the previously obtained orthodontic progression estimate by means of a deep learning model. In a next step an automatic text message is drafted and send to the subject informing him or her about the next step in the treatment. Because of the digital monitoring of the intra-oral image data, there is less need for physical consultations. This saves the subject time and money by reducing the time that the subject has to travel back and forth to the consultation office. Furthermore, it allows the orthodontist to monitor the progress of the treatment more frequently and adjust the treatment scheme faster, significantly reducing the therapy time.

The invention claimed is:

1. A process for initiating, monitoring, and implementing an orthodontic treatment, wherein said orthodontic treatment is a rapid palatal expansion (RPE) treatment comprising:

collecting initial data of a subject requiring orthodontic treatment by an online questionnaire during an initial digital consultation, said initial data comprising at least a digital image of the subject's teeth imaged using a smartphone application, a description of an orthodontic problem and personal information regarding the subject;

selecting the subject that fulfills requirements for the orthodontic treatment based on said initial data of said subject, wherein said requirements comprise the presence of an intra-oral condition in need of the RPE treatment with an initial palatal expander and one or more additional palatal expanders to be used after the initial palatal expander, the presence of which is established by a practitioner based on the digital image of the subject's teeth;

obtaining further data from said subject during an in-person consultation wherein said further data comprises intra-oral image data in the form of a scanned image generated from the oral cavity of said subject, said intra-oral image data being obtained during the in-person consultation by an intra-oral digital scanner;

analysing said intra-oral image data by converting the scanned image of orthodontic anatomy of the subject into a digital three-dimensional (3-D) model of malocclusions of the subject, and providing an initial orthodontic treatment scheme for said subject based on said analysis of said intra-oral image data, said initial orthodontic treatment scheme comprising a treatment in order to obtain a desired orthodontic result and an orthodontic progression estimate;

designing and manufacturing the initial palatal expander, wherein said designing is based on the analysis of the intra-oral image data and the orthodontic progression estimate; and initiating said initial orthodontic treatment scheme for said subject by implementing the initial palatal expander;

wherein a follow up and/or the implementation of said initial orthodontic treatment scheme in said subject is performed in a digital manner, comprising one or more digital treatment consultations characterized in that during said one or more digital treatment consultations, said subject provides additional intra-oral image data imaged using the smartphone application via a digital platform to a practitioner and wherein said additional intra-oral image data uploaded to said digital platform is compared with said orthodontic progression estimate automatically using a machine learning model, and said machine learning model determines whether said initial orthodontic treatment scheme is maintained or amended to thereby provide an amended orthodontic treatment scheme based on said comparison, wherein the comparison with the orthodontic progression estimate compares pixels of said additional intra-oral image data with one or more 3-D digital orthodontic models of said initial orthodontic treatment scheme;

wherein, if said machine learning model determines that said initial orthodontic treatment scheme is amended, the process further comprises:

designing and manufacturing the one or more additional palatal expanders to implement the amended orthodontic treatment scheme; and initiating said amended orthodontic treatment scheme by implementing said one or more additional palatal expanders;

wherein, if said machine learning model determines that said initial orthodontic treatment scheme is maintained, the process further comprises:

maintaining said initial orthodontic treatment scheme with the initial palatal expander.

2. The process according to claim 1, wherein the initial orthodontic treatment scheme or the amended orthodontic treatment scheme is accelerated by one or more accelerating orthodontic devices, wherein each of said accelerating orthodontic device accelerates tooth movement by soft pulse technology or photobiomodulation.

3. The process according to claim 1, wherein said orthodontic progression estimate comprises one or more digital orthodontic models of said subject's orthodontic anatomy, said digital orthodontic models comprises a model of the subject's desired orthodontic result and one or more models of intermediate orthodontic results.

4. The process according to claim 1, wherein a morphing technique is performed to render an immediate result simulation to display the desired orthodontic result and the orthodontic progression estimate.

5. The process according to claim 1, wherein a result of the machine learning model is verified by the practitioner.

6. The process according to claim 1, wherein the smartphone used with the smartphone application includes a built-in camera.

7. The process according to claim 1, wherein, in addition to the effects of the initial orthodontic treatment scheme or the amended orthodontic treatment scheme, additional data related to oral hygiene and periodontal diseases are monitored.

8. The process according to claim 1, wherein after the initial orthodontic treatment scheme or the amended orthodontic treatment scheme, updated additional intra-oral image data is obtained by the subject and processed by an online platform to prevent relapse, by comparing the additional intra-oral image data after the initial orthodontic treatment scheme or the amended orthodontic treatment scheme to the updated additional intra-oral image data.

9. The process according to claim 1, further comprising generating a simulation of a face of the subject as a result of the initial orthodontic treatment scheme for the subject.

* * * * *